US012648734B2

(12) United States Patent
Shelton et al.

(10) Patent No.: US 12,648,734 B2
(45) Date of Patent: Jun. 9, 2026

(54) WAKEFULNESS AND SLEEP STAGE DETECTION USING RESPIRATION EFFORT VARIABILITY

(71) Applicant: The Alfred E. Mann Foundation for Scientific Research, Valencia, CA (US)

(72) Inventors: Brian Michael Shelton, Altadena, CA (US); Sahar Elyahoodayan, Los Angeles, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 34 days.

(21) Appl. No.: 18/940,530

(22) Filed: Nov. 7, 2024

(65) Prior Publication Data

US 2025/0064388 A1 Feb. 27, 2025

Related U.S. Application Data

(63) Continuation of application No. 18/064,113, filed on Dec. 9, 2022, now Pat. No. 12,178,600.

(60) Provisional application No. 63/265,271, filed on Dec. 10, 2021.

(51) Int. Cl.
*A61B 5/00* (2006.01)
*A61B 5/0205* (2006.01)

(52) U.S. Cl.
CPC .......... *A61B 5/4812* (2013.01); *A61B 5/0205* (2013.01); *A61B 5/4809* (2013.01); *A61B 5/6802* (2013.01)

(58) Field of Classification Search
CPC ... A61B 5/4812; A61B 5/0205; A61B 5/4809; A61B 5/6802; A61B 5/02405; A61B 5/0816; A61B 5/113
See application file for complete search history.

(56) References Cited

U.S. PATENT DOCUMENTS

| | | | |
|---|---|---|---|
| 2006/0169282 A1* | 8/2006 | Izumi ................... | A61B 5/4812 |
| | | | 128/204.23 |
| 2012/0179061 A1 | 7/2012 | Ramanan et al. | |
| 2015/0165200 A1* | 6/2015 | Arnold ............... | A61N 1/37247 |
| | | | 607/42 |
| 2016/0151603 A1* | 6/2016 | Shouldice .............. | G16H 20/70 |
| | | | 600/26 |
| 2016/0213309 A1* | 7/2016 | Sannholm ............ | A61B 5/7271 |
| 2018/0078219 A1 | 3/2018 | Selvaraj | |
| 2020/0337634 A1 | 10/2020 | McDarby et al. | |

FOREIGN PATENT DOCUMENTS

JP 2004049838 A 2/2004

OTHER PUBLICATIONS

Guede-Fernandez et al., "Driver Drowsiness Detection Based on Respiratory Signal Analysis," IEEE Access, Jun. 2019, vol. 7, pp. 81826-81838.

(Continued)

*Primary Examiner* — Omeed Alizada
(74) *Attorney, Agent, or Firm* — ARENTFOX SCHIFF LLP

(57) ABSTRACT

The present disclosure generally relates to systems and methods for monitoring and/or the sleep stage of an individual using one or more sensors, and methods of treating medical conditions related thereto (e.g., obstructive sleep apnea).

20 Claims, 5 Drawing Sheets

(56) References Cited

OTHER PUBLICATIONS

International Search Report and Written Opinion in PCT/US2022/081312, mailed Apr. 18, 2023, 16 pages.

G. Gutierrez et al. "Respiratory rate variability in sleeping adults without obstructive sleep apnea", Physiological Reports, vol. 4, Iss. 17, 2016, pp. 1-9.

Nguyen, C. D. et al. "Respiratory variability during Sleep in methadone maintenance treatment patients", Journal of Clinical Sleep Medicine, vol. 12, No. 4, 2016, pp. 607-616.

* cited by examiner

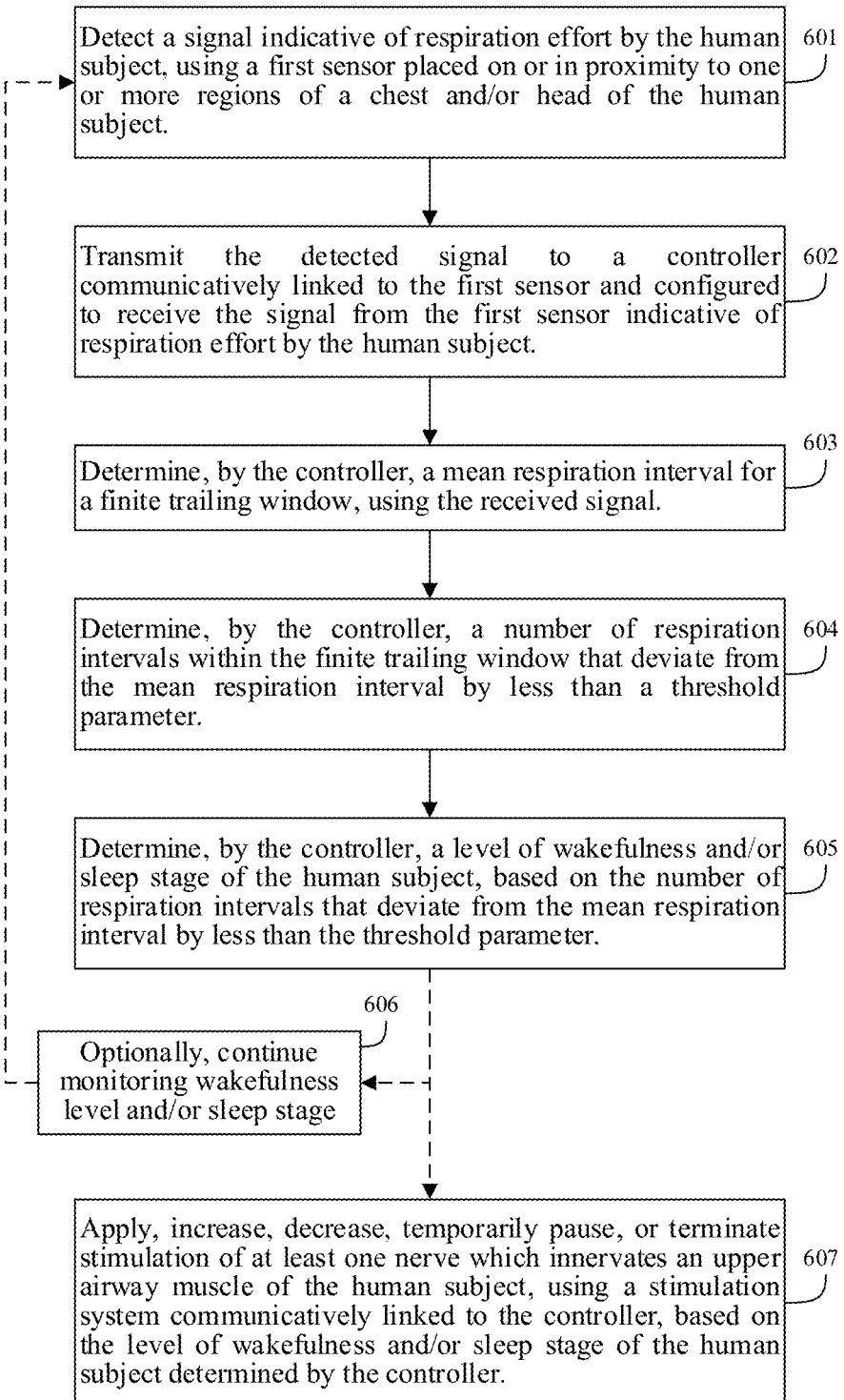

Detect a signal indicative of respiration effort by the human subject, using a first sensor placed on or in proximity to one or more regions of a chest and/or head of the human subject.        601

Transmit the detected signal to a controller communicatively linked to the first sensor and configured to receive the signal from the first sensor indicative of respiration effort by the human subject.        602

Determine, by the controller, a mean respiration interval for a finite trailing window, using the received signal.        603

Determine, by the controller, a number of respiration intervals within the finite trailing window that deviate from the mean respiration interval by less than a threshold parameter.        604

Determine, by the controller, a level of wakefulness and/or sleep stage of the human subject, based on the number of respiration intervals that deviate from the mean respiration interval by less than the threshold parameter.        605

606

Optionally, continue monitoring wakefulness level and/or sleep stage

Apply, increase, decrease, temporarily pause, or terminate stimulation of at least one nerve which innervates an upper airway muscle of the human subject, using a stimulation system communicatively linked to the controller, based on the level of wakefulness and/or sleep stage of the human subject determined by the controller.        607

FIG. 6

WAKEFULNESS AND SLEEP STAGE DETECTION USING RESPIRATION EFFORT VARIABILITY

CROSS-REFERENCE TO RELATED APPLICATION

This application is a continuation of U.S. patent application Ser. No. 18/064,113, filed on Dec. 9, 2022, which claims priority to U.S. Provisional Application No. 63/265,271, filed Dec. 10, 2021, the contents of which are incorporated herein by reference in their entireties.

TECHNICAL FIELD

The present disclosure generally relates to systems and methods for determining and/or monitoring the sleep stage of an individual using one or more sensors, and methods of treating medical conditions related thereto.

BACKGROUND

Obstructive Sleep Apnea (OSA) is a sleep disorder involving obstruction of the upper airway during sleep. The obstruction of the upper airway may be caused by the collapse of or increase in the resistance of the pharyngeal airway, often resulting from tongue obstruction. The obstruction of the upper airway may be caused by reduced genioglossus muscle activity during the deeper states of NREM sleep. Obstruction of the upper airway may cause breathing to pause during sleep. Cessation of breathing may cause a decrease in the blood oxygen saturation level, which may eventually be corrected when the person wakes up and resumes breathing. The long-term effects of OSA include high blood pressure, heart failure, strokes, diabetes, headaches, and general daytime sleepiness and memory loss, among other symptoms.

OSA is extremely common, and may have a prevalence similar to diabetes or asthma. Over 100 million people worldwide suffer from OSA, with about 25% of those people being treated. Continuous Positive Airway Pressure (CPAP) is a conventional therapy for people who suffer from OSA. More than five million patients own a CPAP machine in North America, but many do not comply with use of these machines because they cover the mouth and nose and, hence, are cumbersome and uncomfortable.

Neurostimulators may be used to open the upper airway as a treatment for alleviating apneic events. Such therapy may involve stimulating the nerve fascicles of the hypoglossal nerve (HGN) that innervate the intrinsic and extrinsic muscles of the tongue in a manner that prevents retraction of the tongue which would otherwise close the upper airway during the inspiration period of the respiratory cycle. For example, current stimulator systems may be used to stimulate the trunk of the HGN with a nerve cuff electrode. However, these systems do not provide a sensor or sensing capabilities, and therefore, the stimulation delivered to the HGN trunk is not synchronized to the respiratory cycle or modulated based upon the wakefulness of the individual being treated.

BRIEF SUMMARY OF EXEMPLARY ASPECTS OF THE DISCLOSURE

Ideally, a system for treating OSA should account for the wakefulness of the individual being treated. In most cases, stimulation will only need to be applied when the individual is asleep. Accordingly, a system that accounts for wakefulness may improve battery life by detecting or monitoring wakefulness and then adjusting one or more parameters in response (e.g., one or more sensors may be disabled or switched to a low-power mode when a patient is determined to be awake). Moreover, a system designed to account for wakefulness would be less likely to incorrectly apply stimulation (e.g., a system that accounts for the position or movement of an individual, but not wakefulness, may incorrectly apply stimulation to a patient laying in a supine state while awake). To date, current OSA stimulation systems have failed to provide this functionality, resulting in a need in the art for improved OSA stimulation systems that account for wakefulness as a parameter when selecting or applying stimulation, and in connection with the operation of the system generally.

The present disclosure addresses these and other shortcomings by providing OSA stimulation systems that can accurately detect and/or monitor wakefulness using one or more sensors incorporated into or in communication with the system. Such systems may advantageously display improved power efficiency, accuracy, and/or functionality compared to current systems, among other benefits which will become apparent in view of the following description and the accompanying figures.

In a first general aspect, the disclosure provides a computer-implemented system for determining a level of wakefulness and/or sleep stage of a human subject, comprising: a first sensor configured to detect a signal indicative of respiration effort by the human subject when placed on or in proximity to one or more regions of a chest and/or head of the human subject; and a controller comprising a processor and memory, communicatively linked to the first sensor and configured to receive the signal from the first sensor indicative of respiration effort by the human subject, and to use the received signal to: determine a mean respiration interval for a finite trailing window, and determine a number of respiration intervals within the finite trailing window that deviate from the mean respiration interval by less than a threshold parameter, determine a level of wakefulness and/or sleep stage of the human subject, based on the number of respiration intervals that deviate from the mean respiration interval by less than the threshold parameter.

In some aspects, the first sensor comprises at least one sensor configured to detect a signal indicative of respiration effort comprises an inertial measurement unit ("IMU," e.g., an accelerometer), a microphone, a pressure sensor, a photoplethysmogram ("PPG") sensor, and/or an electrocardiogram ("EKG") sensor. It is expressly contemplated that any of the systems described herein may comprise a plurality of first sensors, each positioned independently on or in proximity to the human subject. The systems described herein may utilize signals from any or all of such sensors when determining the level of wakefulness and/or sleep stage of a human subject.

In some aspects, the system further comprises a second sensor configured to detect a signal indicative of a heart rate of the human subject; and wherein the controller is further configured to receive one or more signals from the second sensor, indicative of the heart rate of the human subject, and to determine a heart rate of the human subject, determine a change in heart rate of the human subject over a period of time, and determine a level of wakefulness and/or sleep stage of the human subject based on both the number of respiration intervals that deviate from the mean respiration interval by less than the threshold parameter and the change in heart rate of the human subject over a period of time. In some aspects, the second sensor comprises an IMU, a pressure sensor, a PPG sensor, and/or an EKG sensor. In some aspects, the second sensor comprises a triaxial accelerometer and a gyroscope. In some aspects, the second sensor is optionally configured to detect both respiration and heart rate of the human subject. It is expressly contemplated that any of the systems described herein may comprise a plurality of second sensors, each positioned independently on or in proximity to the human subject. The systems described herein may utilize signals from any or all of such sensors when determining the level of wakefulness and/or sleep stage of a human subject.

In some aspects, the first and/or second sensors may comprise sensors configured to collect biometric data from a human subject when placed on or in proximity to the subject's body (e.g., on or in proximity to the head, the chest, or any portion thereof). For example, the first sensor may comprise a microphone configured to obtain a respiration effort signal when placed on or in proximity to the subject's chin, and the second sensor may comprise an IMU configured to detect a heart rate signal when placed on or in proximity to the subject's chest. The sensors described herein may be affixed to a subject's body, e.g., using an adhesive, strap, harness, housing or any other means for holding the sensor in contact with or in proximity to the subject. Each sensor, or a combination thereof, may be wholly or partially contained by a housing (e.g., which may contain a batter, memory, a wireless or wired communication system, and other electronic components used to store, process, and/or communicate the signal(s) records by any given sensor). In some aspects, the sensors described herein may be implanted into the human subject (e.g., an implanted OSA stimulation system may include an IMU capable of detecting a signal indicative of the subject's heart rate).

In some aspects, the system may be configured to utilize a threshold parameter that is about or exactly ±0.080, ±0.085, ±0.090, ±0.095, ±0.100, ±0.105, ±0.110, ±0.115, or ±0.120 seconds from the mean respiration interval (e.g., ±0.1 seconds). In some aspects, the threshold parameter is about or exactly ±1.0%, ±1.5%, ±2.0%, ±2.5%, ±3.0%, ±3.5%, ±4.0%, ±4.5%, or ±5.0% from the mean respiration interval.

In some aspects, the controller is further configured to determine the level of wakefulness and/or sleep stage of the human subject, based on a percentage of respiration intervals within the finite trailing window that deviate from the mean respiration interval by less than the threshold parameter. For example, the system may be configured to determine that the subject is awake when 0-40% percent of respiration intervals within the finite trailing window deviate by less than the threshold, in REM sleep when 0-40% percent of respiration intervals within the finite trailing window deviate by less than the threshold, in light sleep when 40-60% percent of respiration intervals within the finite trailing window deviate by less than the threshold, and in deep sleep when >60% percent of respiration intervals within the finite trailing window deviate by less than the threshold. In other aspects, the system may be configured to determine that the subject is awake, in REM sleep, in light sleep, or in deep sleep, when the percentage of respiration intervals within the finite trailing window falls within a range defined by any combination of endpoints selected from 10, 20, 30, 40, 50, 60, 70, 80, 90, and 100% (e.g., the ranges described above in this passage are merely exemplary). In some aspects, the thresholds may be determined based on a prior sleep study conducted for the subject. In others, the thresholds may be empirical determined, e.g., based on one or more test populations.

In some aspects, the controller is further configured to identify respiration intervals by: a) identifying any unique point on two or more consecutive periods of a respiration waveform generated from the received one or more signals from the first sensor; b) identifying consecutive peaks of a respiration waveform generated from the received one or more signals from the first sensor, and measure the time between these peaks; and/or c) identifying consecutive troughs of a respiration waveform generated from the received one or more signals from the first sensor, and measure the time between these troughs; and/or d) identifying any unique point on two or more consecutive periods of a respiration waveform generated from the received one or more signals from the first sensor; and/or e) identifying consecutive points of maximum or minimum rates of change of a respiration waveform generated from the received one or more signals from the first sensor, and measure the time between these points.

In some aspects, the controller is further configured to identify respiration intervals by: removing one or more low-frequency components of a respiration waveform generated from the received one or more signals from the first sensor; and measuring the time between two consecutive positive or negative zero crossings. In some aspects, the controller may be configured to analyze signals within the range of 0.1 to 0.67 Hz.

In some aspects, the level of wakefulness and/or sleep stage of the human subject comprises a determination that the human subject is awake, in light sleep, in deep sleep, in REM sleep, or in an N1, N2, or N3 sleep stage.

In some aspects, the controller is further configured to modify the threshold parameter based on: a) a physical orientation of the human subject; and/or b) a mean respiration interval for a prior finite trailing window. For example, the system may be configured to store respiration interval data (e.g., the original signal, processed data comprising actual or mean respiration interval values) for a first trailing window and a second trailing window, which may optionally overlap. The second trailing window may, e.g., include earlier time points and serve as a point of comparison to allow the controller to determine whether the mean respiration interval has increased or decreased over a given time interval.

In some aspects, the controller is further configured to determine the change in heart rate of the human subject over a period of time based on a past mean heart rate value for the human subject. For example, the system may be configured to store heart rate data (e.g., the original signal, processed data comprising actual or mean heart rate values). Prior actual or mean values may be used, e.g., to determine whether the subject's heart rate has increased or decreased over a given time interval.

In a second general aspect, the disclosure provides a system for treating obstructive sleep apnea, comprising: any of the computer-implemented systems for determining a level of wakefulness and/or sleep stage of a human subject, as described herein, and a stimulation system, communicatively linked to the controller and configured to deliver stimulation to a nerve which innervates an upper airway muscle of the human subject based on the level of wakefulness and/or sleep stage of the human subject determined by the controller.

In some aspects, the controller is configured to cause the stimulation system to apply, increase, decrease, temporarily pause, or terminate the stimulation based on the level of wakefulness and/or sleep stage of the human subject. In some aspects, the controller is configured to cause the stimulation system to change an amplitude, pulse width, duty cycle, stimulation duration, and/or frequency of the stimulation based on the level of wakefulness and/or sleep stage of the human subject.

In a third general aspect, the disclosure provides a method for determining a level of wakefulness and/or sleep stage of a human subject using any of the computer-implemented systems for determining a level of wakefulness and/or sleep stage of a human subject, as described herein. For example, a method for determining a level of wakefulness and/or sleep stage of a human subject, comprising: a) detecting a signal indicative of respiration effort by the human subject, using a first sensor placed on or in proximity to one or more regions of a chest and/or head of the human subject; b) transmitting the detected signal to a controller communicatively linked to the first sensor and configured to receive the signal from the first sensor indicative of respiration effort by the human subject; c) determining, by the controller, a mean respiration interval for a finite trailing window, using the received signal; d) determining, by the controller, a number of respiration intervals within the finite trailing window that deviate from the mean respiration interval by less than a threshold parameter; and e) determining, by the controller, a level of wakefulness and/or sleep stage of the human subject, based on the number of respiration intervals that deviate from the mean respiration interval by less than the threshold parameter. In the interests of conciseness, not every permutation of such methods are described herein. For example, it should be understood that such methods may utilize any configuration of the systems described herein. Moreover, embodiments are contemplated wherein a single determination is made, as well as embodiments wherein the subject's level of wakefulness and/or sleep stage is monitored over time. For example, in some aspects the system may be configured to repeat any or all of these steps (e.g., the system may be configured to monitor the subject's level of wakefulness and/or sleep stage overnight).

In a fourth general aspect, the disclosure provides methods for treating OSA using any of the computer-implemented systems for determining a level of wakefulness and/or sleep stage of a human subject described herein. For example, a method for treating OSA may comprise a) detecting a signal indicative of respiration effort by the human subject, using a first sensor placed on or in proximity to one or more regions of a chest and/or head of the human subject; b) transmitting the detected signal to a controller communicatively linked to the first sensor and configured to receive the signal from the first sensor indicative of respiration effort by the human subject; c) determining, by the controller, a mean respiration interval for a finite trailing window, using the received signal; d) determining, by the controller, a number of respiration intervals within the finite trailing window that deviate from the mean respiration interval by less than a threshold parameter; e) determining, by the controller, a level of wakefulness and/or sleep stage of the human subject, based on the number of respiration intervals that deviate from the mean respiration interval by less than the threshold parameter; and f) applying, increasing, decreasing, temporarily pausing, or terminating stimulation of at least one nerve which innervates an upper airway muscle of the human subject, using a stimulation system communicatively linked to the controller, based on the level of wakefulness and/or sleep stage of the human subject determined by the controller. In some aspects, the system may be configured to repeat any or all of these steps (e.g., the system may be configured to monitor the subject's level of wakefulness and/or sleep stage overnight and to modulate, apply, or cease stimulation as needed based on changes in the subject's level of wakefulness and/or sleep stage).

It is understood that any of the systems described herein may be configured to store, output, and/or transmit any of the data or parameters described herein. For example, the system may be configured to store actual and/or mean respiratory interval data for the human subject, and/or to output or transmit it to another local or remote device (e.g., a tablet computer or a discrete external controller communicatively linked with the system). In some aspects, the system may be configured to transmit such data to an external server or other local or remote storage (e.g., to archive such data or to provide it to a medical professional for further review). Accordingly, the systems described herein may incorporate a wired or wireless communication means (e.g., Bluetooth or wireless connectivity). The systems described herein may further be configured to allow a user, medical professional, or other party to modify one or more parameters of the system (e.g., the threshold parameter used to determine wakefulness level or sleep stage may be configurable by a medical professional). Updated parameters may be entered manually (e.g., using a dedicated external controller or paired computer or tablet) or received, e.g., as an updated configuration file provided wirelessly from a remote user.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

FIG. 6 is a conceptual flow diagram showing a method for determining a level of wakefulness and/or sleep stage of a human subject. As illustrated by this figure, such methods may optionally include a step wherein the determined wakefulness level and/or sleep stage is used to guide treatment.

Figure 1:
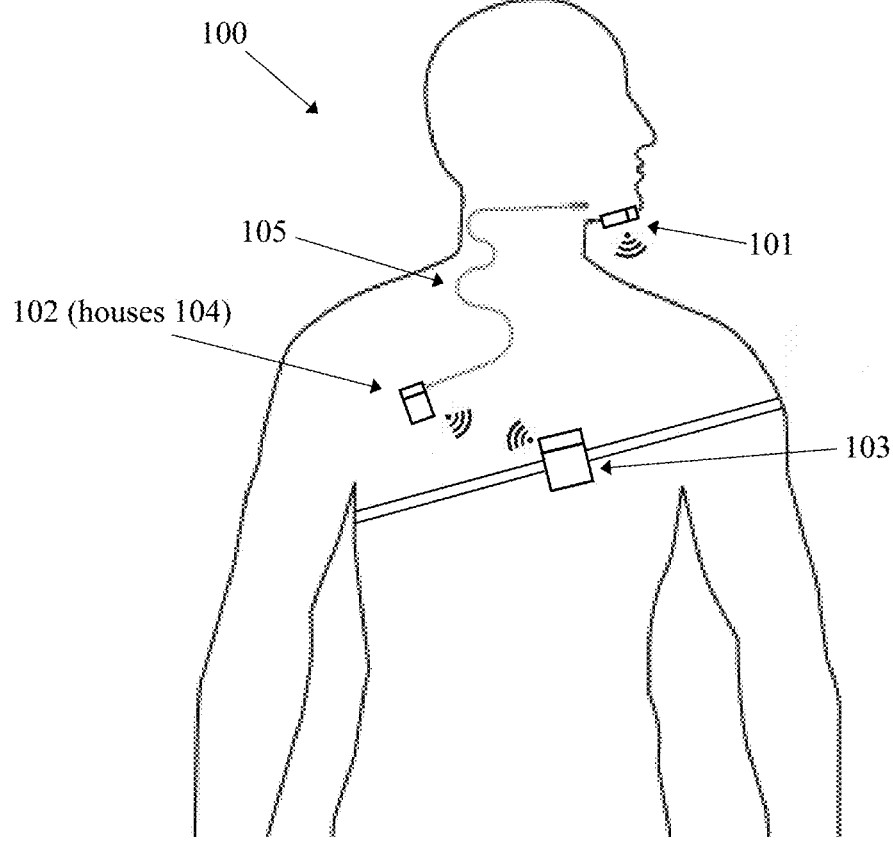
FIG. 1 is a diagram illustrating an exemplary embodiment of a system for treating OSA using wakefulness and/or sleep stage data obtained from a human subject. In this example, the system includes a first sensor (101) attached to the subject's chin (e.g., via an adhesive or strap) and a second sensor (103) comprising a chest-worn IMU (held in place by a strap or harness).

This figure also illustrates an optional embodiment wherein the system is configured to repeat one or more steps (e.g., to monitor the subject's level of wakefulness and/or sleep stage over time).

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Several aspects of exemplary embodiments according to the present disclosure will now be presented with reference to various systems and methods. These systems and methods will be described in the following detailed description and illustrated in the accompanying drawings by various blocks, components, circuits, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented as a "processing system" that includes one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FP-GAs), programmable logic devices (PLDs), application-specific integrated circuits (ASICs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more exemplary embodiments, the functions described may be implemented in hardware, software, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EE-PROM), optical disk storage, magnetic disk storage, other magnetic storage devices, combinations of the aforementioned types of computer-readable media, or any other medium that can be used to store computer executable code in the form of instructions or data structures that can be accessed by a computer.

As explained above, the systems and methods provided herein may be used to determine (and/or monitor) a human subject's wakefulness level or sleep stage, and optionally to treat OSA. OSA stimulation systems according to the disclosure possess several advantages compared to prior systems, and in particular allow for more accurate tailoring of stimulation based parameters, and power savings (e.g., components of the OSA stimulation system may be disabled or switched to a low-power mode when a subject is found to be awake or in a sleep stage wherein stimulation is reduced or unnecessary). Moreover, the present systems are advantageous in that they do not require invasive or uncomfortable sensors, improving the likelihood of patient compliance and positive therapeutic outcomes.

Prior systems based on EKG and electrooculography ("EOG") provide a reliable way to detect wakefulness and sleep stage. However, such systems require many wires and instrumentation that can interfere with sleep. In contrast, OSA stimulation systems according to the disclosure may be able to detect sleep stage and wakefulness in order to be able to automatically start and stop (or otherwise modulate) treatment and to determine sleep quality. The paper "Respiratory rate variability in sleeping adults without obstructive sleep apnea" (G. Gutierrez et al, *Physiol. Rep.,* 4:17, 2016) (hereinafter, "Gutierrez 2016") describes an approach for using nasal cannula pressure respiration rate variability to determine wakefulness. However, this approach requires the use of a nasal cannula or nasal thermistor, which can also impede sleep. Moreover, the technique described in Gutierrez 2016 requires computation of fast Fourier transformations ("FFTs," a processor-intensive calculation) and only produce a sleep stage prediction every 2.7 seconds. Gutierrez's FFT-based technique computes the normalized amount of power that is not in the frequency interval containing the dominant respiration rate. This publication refers to faster, statistical techniques used in another paper, Nguyen et al. "Respiratory variability during Sleep in methadone maintenance treatment patients," *J. Clin. Sleep Med.* 2016. 12:607-616 (hereinafter, "Nguyen 2016"). Gutierrez indicates that Nguyen's technique is not sensitive to determine sleep stage. The Nguyen technique computes the standard deviation of the respiration rate about the mean value. Thus, Nguyen's technique does not apply equal weighting to all values that are more than a small distance from the mean.

In contrast to these prior studies, the present systems and methods utilize a time domain analysis to compute respiration amplitude and rate and respiration amplitude and rate variability in a more energy-efficient manner (e.g., which avoids the need to calculate periodic FFTs). In some aspects, such systems and methods further utilize one of a number of weighting techniques that provides a more uniform weighting distribution for values away from the mean respiration rate and amplitude. In addition, in some aspects adaptive thresholding is used to identify deviation in respiratory rate and amplitude and/or heart rate based on previously computed mean value(s).

A signal indicative of a subject's respiratory cycle may be collected using a first sensor positioned on or in proximity to the subject body (e.g., on or in proximity to the chest or head). In some aspects, the first sensor is an IMU (e.g., an accelerometer), a microphone, or an EKG sensor to detect respiration effort from either the chest or the chin. The respiration effort signal may be filtered to remove noise (e.g., caused by motion). In some aspects, systems according to the disclosure may collect respiration effort using a plurality of sensors (e.g., the first sensor may comprise two or more sensors placed on or in proximity to the subject). Signal data from multiple sensors may subject to sensor fusion or other processing techniques.

As explained above, system may include a controller configured to determine a mean respiration interval for a finite trailing window, using the detected respiratory signal data, and further to determine a number (e.g., a percentage) of respiration intervals within the finite trailing window that deviate from the mean respiration interval by less than a threshold parameter. In some aspects, the system may be configured to utilize a threshold parameter that is about or exactly ±0.080, ±0.085, ±0.090, ±0.095, ±0.100, ±0.105, ±0.110, ±0.115, or ±0.120 seconds from the mean respiration interval.

In some aspects, a threshold parameter of about ±0.100 seconds may be preferable. In Gutierrez (2016), a 100 Hz sampling frequency was used. Thus, the maximum frequency of the FFT was 50 Hz. Each FFT used 214 samples, thus each frequency band was 3 mHz wide. With a 4 second respiration rate, this would equate to 0.25±0.003 Hz or 0.247 to 0.253 Hz. This is a time window of 3.953 to 4.049 seconds, or about 0.1 seconds. By computing the mean breathing interval of a finite trailing window and measuring the number of breathing intervals that fall outside of ±0.1 seconds from that mean, the present systems and methods provide a level of accuracy comparable to that described in Gutierrez (2016) while avoiding the need for energy-intensive FFT calculations.

In some aspects, a controller of the systems described herein may be configured to process the respiratory effort signal data using one or more weighting techniques to provide a more uniform weighting distribution for values away from the mean respiration rate and amplitude (e.g., weightings do not necessarily need to be flat). For example, the sum of logarithmically-weighted differences of respiration intervals from the mean respiration interval may be computed. In some aspects, the controller may be configured to divide the differences by 0.1 seconds before performing the logarithm. Doing so would give small positive weights for values more than 0.1 second away from the mean and large negative weights for values less than this distance from the mean. In instances where there is little variation, this will produce a negative sum, and in instances with large variation, this would produce a positive sum. Accordingly, such techniques provide the advantage of large selectivity when there is little variation. In some aspects, a flat weighting may be applied, e.g. the controller may be configured to count the number of respiration intervals within a desired interval surrounding the mean.

Respiration intervals can be determined using several different techniques, as described above. For example, in some aspects the controller may be configured to identify respiration intervals by: a) identifying any unique point on two or more consecutive periods of a respiration waveform generated from the received one or more signals from the first sensor; b) identifying consecutive peaks of a respiration waveform generated from the received one or more signals from the first sensor, and measure the time between these peaks; and/or c) identifying consecutive troughs of a respiration waveform generated from the received one or more signals from the first sensor, and measure the time between these troughs; and/or d) identifying any unique point on two or more consecutive periods of a respiration waveform generated from the received one or more signals from the first sensor; and/or e) identifying consecutive points of maximum or minimum rates of change of a respiration waveform generated from the received one or more signals from the first sensor, and measure the time between these points. In some aspects, the controller is further configured to identify respiration intervals by removing one or more low-frequency components of a respiration waveform generated from the received one or more signals from the first sensor; and measuring the time between two consecutive positive or negative zero crossings.

Because removing the low frequency components requires a significant amount of processing, in some aspects it may be preferable to track the minimum and maximums of the each cycle of the waveform. Every time a minimum and maximum are detected, a midpoint threshold can be computed. This threshold may then be used to detect the time between the last threshold crossing and two crossings before. If the respiration signal is stable, the threshold computed from a previous half-respiration-interval can be used for detecting the zero crossing of the current half-respiration-interval. However, since the sleep stage computation does not need to be computed within one respiration interval, it is desirable to compute the zero crossing times after-the-fact, once the minimum or maximum is identified and the new threshold is computed.

Once a respiration rate is computed for the most recent respiration interval, it is possible to compute the mean for the previous N respiration intervals. Once the mean respiration interval is computed, upper and lower bounds (e.g., ±0.1 s or ±2.5%), can be computed. Then, the percentage of respiration cycles within these bounds can be counted. Re-computing these variables for each respiration cycle will typically provide the fastest sleep-stage update. However, if processing time needs to be reduced, in some aspects the computation of the mean, bounds, and in-bound respiration percentage can be performed at some periodic interval (e.g. every 30 seconds), in order to correspond to a sleep epoch.

In some aspects, the correlation between respiration variability (i.e., the percentage of in-band respiration cycles) and a given sleep stage may be subject and time independent. In such cases, the correlation can thus be computed ahead of time and incorporated into the detection algorithm applied by the systems described herein. For example, the Awake, REM, N1, N2, and N3 sleep stages may each correlate with a percentage of respiration intervals falling within a different range (e.g., the Awake and REM states may correlate with 20-40% and 40-60% of respiration intervals deviating by less than the threshold, respectively). However, in some aspects the systems described herein may be configured to address subject variability (e.g., different thresholds for different human subjects). These thresholds may be computed, e.g., as part of a one-time sleep study for the subject wherein EKG and EOG data is collected and scored for sleep stage. If the respiration variability to sleep stage correlation changes over time for a particular subset of subjects, this mapping of percentages to sleep stages may be re-assessed with additional sleep studies. Averages can be computed for the percent of respiration intervals in the window for each transition between any two sleep stages. These averages could then be used to delineate sleep stages. This would work well if a sleep study can be performed. However, it may be desirable to adjust these thresholds without using a sleep study. In this case, the threshold dividing Awake to N1 can be determined without a full study. This could be done, e.g., by looking for the minimum value while the patient is awake and the maximum value shortly after stimulation starts. The average of these values may be used as the new awake to N1 threshold. The ratio of the change in thresholds may be computed and used to scale all thresholds using this singular scaling factor.

As noted above, the systems and methods described herein may account for the physical orientation of the human subject. Respiratory amplitude becomes shallower as a subject shifts from wakefulness to deep sleep. However, respiratory amplitude measured by an IMU or sound is also a function of subject's physical orientation. Therefore, in some aspects physical orientation as well as past mean respiratory amplitude may be used to adjust the threshold used to determine the subject's wakefulness level or sleep stage, resulting in an adaptive threshold.

The systems and methods described herein may utilize one or more sensors configured to detect respiratory effort data, e.g., the first sensor described in several embodiments herein. However, in other aspects, such systems may also collect heart rate data using a second sensor. For example, the subject's heart rate may be determined using a chest-worn IMU and its variability may be correlated to sleep stage (i.e., heart rate drops from wakefulness to deep sleep). A human subject's heart rate typically lies between 40 to 200 beats per minute, which corresponds to 0.67 Hz to 3.33 Hz. In some aspects, the system may incorporate a Butterworth filter may be applied to keep the signal component within this spectrum. The subject's heart rate may be calculated as the peak-to-peak difference multiplied by 60. Changes in heart rate calculated based on past mean rate values correspond to sleep stage. In light sleep, a subject's heart rate drops slightly to what is known as their resting heart rate. In deep sleep, the heart rate drops another 20-30% compared to the resting heart rate. In instances where a subject wakes up due to a sleep apnea, the activation of the sympathetic nervous system relates to an increased heart rate and heart rate variability. Thus, in some aspects, the controller of the systems described herein may be configured to use heart rate in combination with respiration rate, e.g., to detect a sleep apnea and/or determine treatment parameters.

FIG. 1 is a diagram illustrating an exemplary embodiment of a system for treating OSA (100) using wakefulness and/or sleep stage data obtained from a human subject. In this example, the system includes a first sensor (101) attached to the subject's chin (e.g., via an adhesive or strap) and a second sensor (103) comprising a chest-worn IMU (held in place by a strap or harness). Both sensors are communicatively linked to an implanted OSA stimulation system. In this exemplary embodiment, the implanted OSA stimulation system comprises a housing (102) that includes both an implantable pulse generator ("IPG") and a controller (104) configured to handle signal processing and storage, operation of the OSA stimulation system, and wireless communication between the OSA stimulation system and the external sensors (e.g., the first sensor (101) and the second sensor (103)). The OSA stimulation system further includes one or more electrodes (105) to deliver stimulation to one or more nerves which innervate an upper airway muscle of the human subject. As described herein, the system (100) may be used to treat OSA based upon the subject's level of wakefulness or sleep stage, which may be determined by the controller (104) using any of the techniques described herein.

Figure 2:
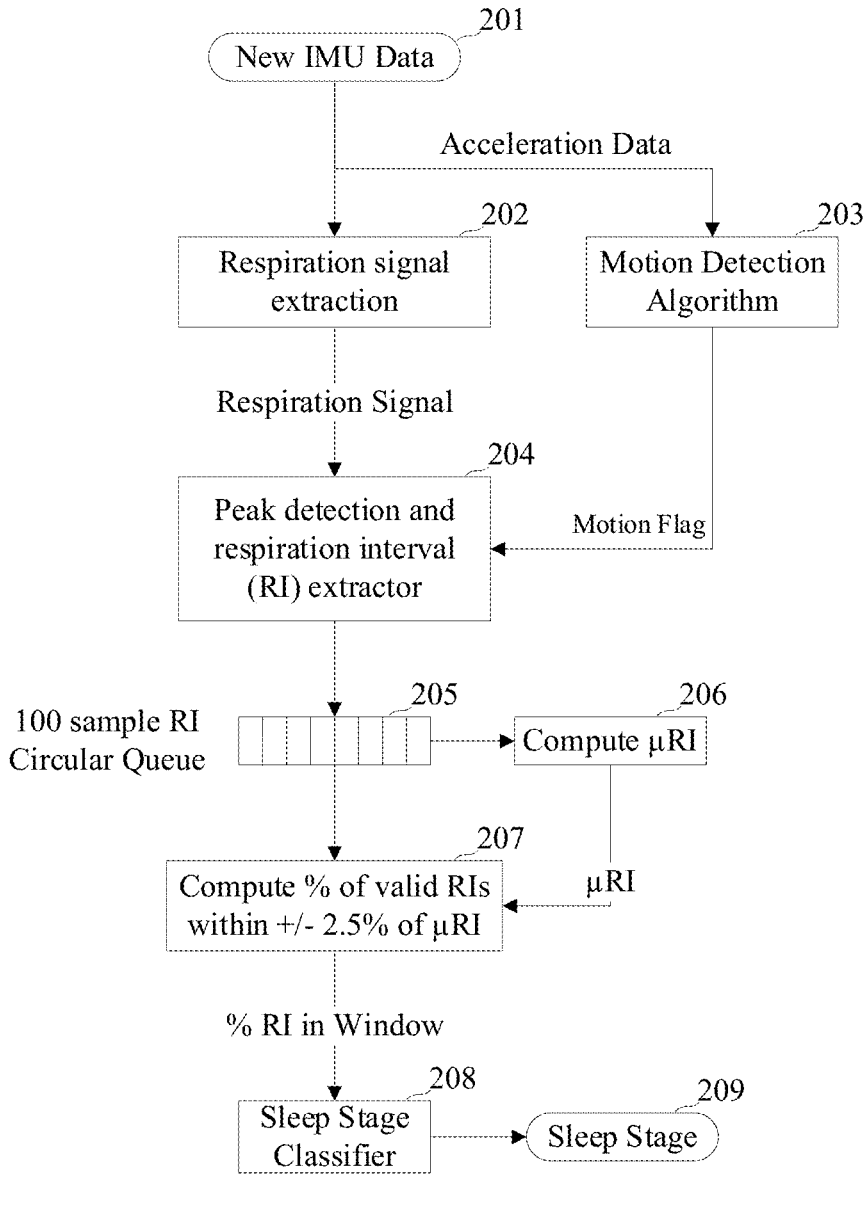
FIG. 2 is a conceptual flow diagram summarizing a method for determining a wakefulness level and/or sleep stage of human subject using an exemplary system according to the disclosure.

FIG. 2 is a conceptual flow diagram summarizing a method for determining a wakefulness level and/or sleep stage of human subject using an exemplary system according to the disclosure. As illustrated by this figure, at step 201 the controller of a system according to the disclosure may receive a signal from an IMU placed on or in proximity to the human subject (e.g., a chin-worn IMU). A respiration signal may be extracted from the received signal (step 202) and acceleration can be processed using a motion detection algorithm (step 203). The controller may then proceed to detect peaks in the respiration signal and to determine respiratory intervals for the human subject, based on the signal (step 204). As shown by this figure, the controller may be configured to trigger a motion flag, e.g., when the acceleration data shows that the patient is moving or has recently moved. The controller may be configured to take this flag into account, e.g., by pausing further processing of the respiration signal until the subject is no longer mobile. At step 205, the controller may proceed to save respiratory interval data for a finite trailing window. Here, the controller is shown using a circular queue to store data for the 100 most recent respiratory intervals.

The controller may be configured to compute a mean respiratory interval (step 206) and to use this mean to compute a percentage of respiratory intervals in the finite trailing window which fall within a given threshold, in this case ±2.5% from the mean respiratory interval (step 207). Note that in this particular example, the flow diagram indicates that only valid respiration intervals are considered in the foregoing analysis. The controller may be configured to flag respiratory intervals as being valid or invalid, e.g., based on whether or not a motion flag was detected for the time point of a given respiratory interval, or based on any other criteria. Upon determining the percentage of respiratory intervals in the finite trailing window which satisfy the threshold, the controller may then proceed to determine the human subject's wakefulness level or sleep stage (step 208). The determined wakefulness level or sleep stage may then be used (e.g., to guide OSA stimulation), saved, output, or transmitted (step 209).

Figure 3:
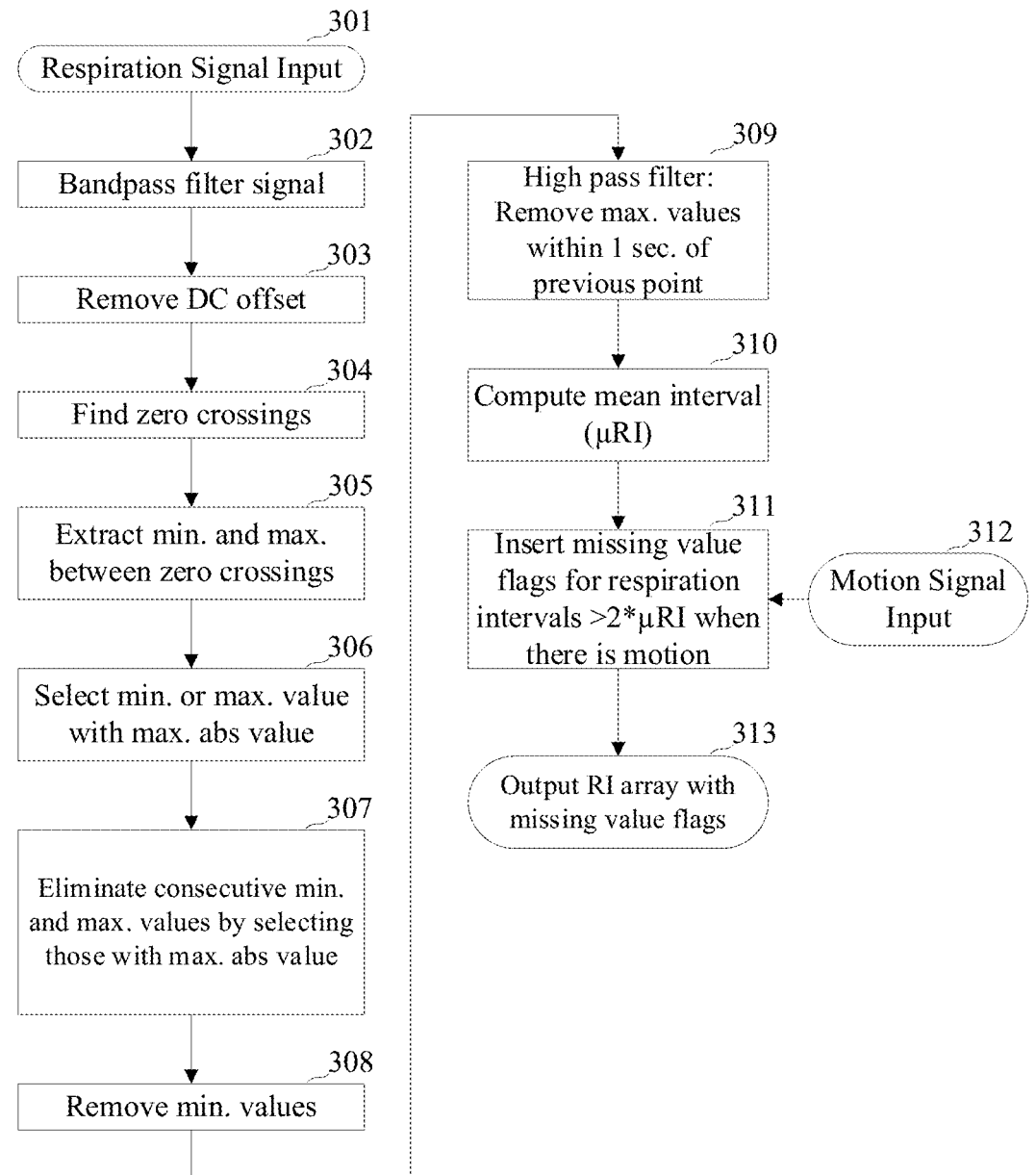
FIG. 3 is a conceptual flow diagram summarizing a method for processing a signal indicative of respiration effort detected by one or more sensors of the systems described herein.

FIG. 3 is a conceptual flow diagram summarizing a method for processing a signal indicative of respiration effort detected by one or more sensors of the systems described herein. This figure provides additional detail regarding the processing that may be performed, e.g., during steps 201-204 shown in FIG. 2. As shown by this flow diagram, signal processing may begin with the receipt of a respiration signal by the controller (step 301), which may then be subjected to a bandpass filter (step 302) and processing to remove the DC offset (step 303). The controller may then proceed to find the zero crossing (Step 304), to extract the minimum and maximum values between zero crossings (step 305), and to select minimum or maximum values with maximum absolute value (step 306). Consecutive minimum and maximum values may be eliminated by selecting those with maximum absolute value (step 307), and minimum values may be removed (step 308). At step 309, the signal may then be subjected to a high pass filter to remove maximum values within a given threshold of the previous point (e.g., within 1 second of the previous point), and a mean respiratory interval may then be computed (step 310). At step 311, missing value flags may then be inserted for respiration intervals greater than a given threshold multiplied by the mean respiratory interval (e.g., 2× the mean respiratory interval, in this case), when motion is detected by an IMU or other sensor (provided at step 312). Finally, a respiratory interval array with missing value flags is generated at step 312 (e.g., the 100-sample respiratory interval circular queue shown in FIG. 2).

Figures 4, 5:
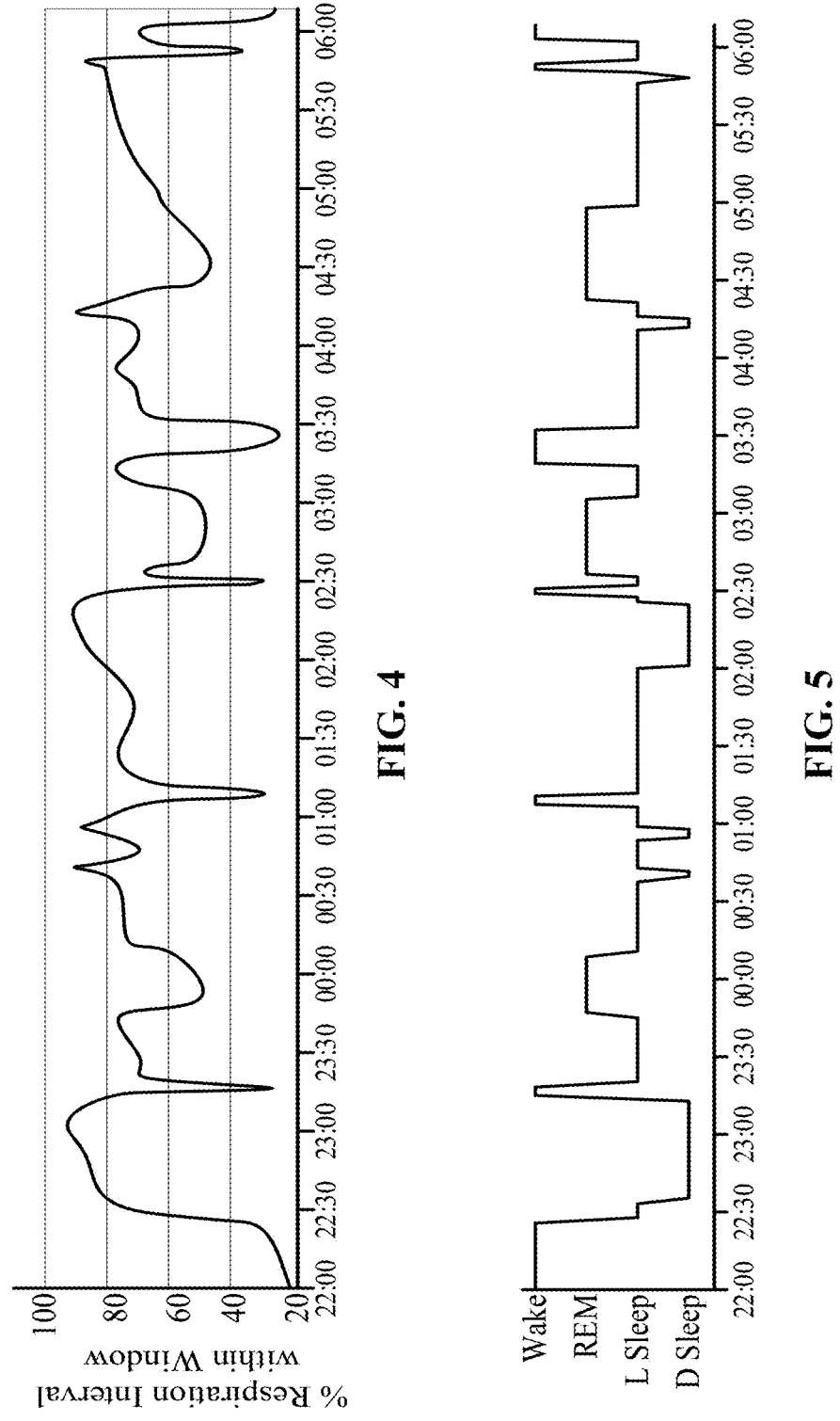
FIG. 4 is a graph showing the percentage of respiratory intervals within a finite trailing window which fall within a preset threshold, based on data collected from a hypothetical human subject using a system as described herein.
FIG. 5 is graph showing wakefulness level or sleep stage assignments for the human subject, based on the respiratory interval percentage data shown in FIG. 4.

FIG. 4 is a graph showing the percentage of respiratory intervals within a finite trailing window which fall within a preset threshold, based on data collected from a hypothetical human subject using a system as described herein. FIG. 5 is graph showing wakefulness level or sleep stage assignments for the human subject, based on the respiratory interval percentage data shown in FIG. 4. In some aspects, the thresholds for each wakefulness level or sleep stage may vary (e.g., based on the subject, time, or other factors). The assignments shown here are merely exemplary.

FIG. 6 is a conceptual flow diagram showing a method for determining a level of wakefulness and/or sleep stage of a human subject. As illustrated by this figure, such methods may optionally include a step wherein the determined wakefulness level and/or sleep stage is used to guide treatment. This figure also illustrates an optional embodiment wherein the system is configured to repeat one or more steps (e.g., to monitor the subject's level of wakefulness and/or sleep stage over time).

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. A computer-implemented system for determining a level of wakefulness and/or sleep stage of a human subject, comprising:
a first sensor configured to detect a signal indicative of respiration effort by the subject when placed on or in proximity to one or more regions of a chest and/or head of the subject; and a controller comprising a processor and memory, communicatively linked to the first sensor and configured to receive the signal from the first sensor indicative of respiration effort by the subject, and to use the received signal to:
determine a physical orientation of the subject, based on a respiratory amplitude of the subject identified using the signal from the first sensor;
determine a mean respiration interval for the subject, based on a plurality of respiration intervals identified using the signal from the first sensor;
determine a level of wakefulness and/or sleep stage of the subject, based on a percentage of respiration intervals within a first defined time period that deviate from the mean respiration interval by less than a threshold parameter, wherein the threshold parameter is based in part on the subject's orientation.

2. The system of claim 1, wherein the level of wakefulness and/or sleep stage comprises a determination that the subject is awake, in light sleep, in deep sleep, in REM sleep, or in an N1, N2, or N3 sleep stage.

3. The system of claim 2, wherein each level of wakefulness and/or sleep stage corresponds to a different percentage range of respiration intervals within the first defined time period that deviate from the mean respiration interval by less than the threshold parameter.

4. The system of claim 1, wherein the system further comprises
a second sensor configured to detect a signal indicative of a heart rate of the subject; and wherein:
the controller is further configured to:
determine a heart rate of the subject using the signal detected by the second sensor,
determine a change in the heart rate of the subject over a second defined time period, which may be the same as or different from the first defined time period, and
determine a level of wakefulness and/or sleep stage of the subject based on both the number of respiration intervals within the first defined time period that deviate from the mean respiration interval by less than the threshold parameter and the change in the heart rate of the subject during the second defined time period.

5. The system of claim 1, wherein the first sensor comprises at least one sensor configured to detect a signal indicative of respiration effort comprises an inertial measurement unit ("IMU"), a microphone, a pressure sensor, a photoplethysmogram ("PPG") sensor, and/or an electrocardiogram ("EKG") sensor.

6. The system of claim 3, wherein the second sensor comprises an IMU, a pressure sensor, a PPG sensor, and/or an EKG sensor; optionally wherein the second sensor is configured to detect both respiration and heart rate of the subject.

7. The system of claim 6, wherein the second sensor comprises a triaxial accelerometer and a gyroscope.

8. The system of claim 4, wherein:
a) the first sensor is configured to be positioned on the chest and/or chin of the subject;
b) the second sensor is a chest-worn IMU; and/or
c) the first sensor and/or the second sensor is an implantable sensor.

9. The system of claim 1, wherein the controller is further configured to identify respiration intervals by:
a) identifying any unique point on two or more consecutive periods of a respiration waveform generated from the received one or more signals from the first sensor;

b) identifying consecutive peaks of a respiration wave-form generated from the received one or more signals from the first sensor, and measure the time between these peaks; and/or c) identifying consecutive troughs of a respiration wave-form generated from the received one or more signals from the first sensor, and measure the time between these troughs; and/or d) identifying any unique point on two or more consecutive periods of a respiration waveform generated from the received one or more signals from the first sensor; and/or e) identifying consecutive points of maximum or minimum rates of change of a respiration waveform generated from the received one or more signals from the first sensor, and measure the time between these points.

10. A system for treating obstructive sleep apnea, comprising:

the computer-implemented system for determining a level of wakefulness and/or sleep stage of a subject, of claim 1, and a stimulator, communicatively linked to the controller and configured to deliver electrical stimulation to a nerve which innervates an upper airway muscle of the subject based on the level of wakefulness and/or sleep stage of the subject determined by the controller.

11. The system of claim 10, wherein the controller is configured to cause the stimulator to apply, increase, decrease, temporarily pause, or terminate the stimulation based on the level of wakefulness and/or sleep stage of the subject.

12. The system of claim 11, wherein the controller is configured to cause the stimulator to change an amplitude, pulse width, duty cycle, stimulation duration, and/or frequency of the stimulation based on the level of wakefulness and/or sleep stage of the subject.

13. A method for determining a level of wakefulness and/or sleep stage of a human subject, comprising:

a) detecting a signal indicative of respiration effort by the subject, using a first sensor placed on or in proximity to one or more regions of a chest and/or head of the subject;

b) transmitting the detected signal to a controller communicatively linked to the first sensor;

c) determining, by the controller, a physical orientation of the subject, based on a respiratory amplitude of the subject determined using the signal from the first sensor d) determining, by the controller, a mean respiration interval for the subject, based on a plurality of respiration intervals identified using the signal from the first sensor;

e) determining, by the controller, a level of wakefulness and/or sleep stage of the subject, based on a percentage of respiration intervals within a first defined time period that deviate from the mean respiration interval by less than a threshold parameter, wherein the threshold parameter is based in part on the subject's orientation.

14. The system of claim 13, wherein the level of wakefulness and/or sleep stage comprises a determination that the subject is awake, in light sleep, in deep sleep, in REM sleep, or in an N1, N2, or N3 sleep stage.

15. The system of claim 14, wherein each level of wakefulness and/or sleep stage corresponds to a different percentage range of respiration intervals within the first defined time period that deviate from the mean respiration interval by less than the threshold parameter.

16. The method of claim 13, further comprising:

f) applying, increasing, decreasing, temporarily pausing, or terminating electrical stimulation of at least one nerve which innervates an upper airway muscle of the subject, using a stimulator communicatively linked to the controller, based on the level of wakefulness and/or sleep stage of the subject.

17. The method of claim 16, where step f) further comprises changing an amplitude, pulse width, duty cycle, stimulation duration, and/or frequency of the electrical stimulation based on the level of wakefulness and/or sleep stage of the subject.

18. The method of claim 13, wherein the first sensor comprises at least one sensor configured to detect a signal indicative of respiration effort comprises an inertial measurement unit ("IMU"), a microphone, a pressure sensor, a photoplethysmogram ("PPG") sensor, and/or an electrocardiogram ("EKG") sensor.

19. The method of claim 13, wherein the system further comprises a second sensor configured to detect a signal indicative of a heart rate of the subject; and wherein:

the controller is further configured to:

determine a heart rate of the subject using the signal detected by the second sensor, determine a change in heart rate of the subject over a second defined time period, which may be the same as or different from the first defined time period, and determine a level of wakefulness and/or sleep stage of the subject based on both the number of respiration intervals within the first defined time period that deviate from the mean respiration interval by less than the threshold parameter and the change in the heart rate of the subject during the second defined time period.

20. The method of claim 19, wherein the second sensor comprises an IMU, a pressure sensor, a PPG sensor, and/or an EKG sensor; optionally wherein the second sensor is configured to detect both respiration and heart rate of the subject.

* * * * *